(12) United States Patent
Wang (10) Patent No.: US 6,573,042 B1
(45) Date of Patent: Jun. 3, 2003

(54) DETECTION OF BLADDER CANCER

(75) Inventor: Mary Ge Wang, Rockville, MD (US)

(73) Assignee: Oncor, Inc., Gaithersburg, MD (US)

( * ) Notice: Subject to any disclaimer, the term of this patent is extended or adjusted under 35 U.S.C. 154(b) by 0 days.

(21) Appl. No.: 08/729,199

(22) Filed: Oct. 15, 1996

Related U.S. Application Data (63) Continuation of application No. 08/330,239, filed on Oct. 27, 1996, now abandoned, which is a continuation of application No. 08/151,445, filed on Nov. 12, 1993, now abandoned.

(51) Int. Cl.$^7$ .............................. C12Q 1/68; C12P 19/34
(52) U.S. Cl. ........................................... 435/6; 435/91.2
(58) Field of Search ..................... 435/6, 91.2; 436/813

(56) References Cited

PUBLICATIONS

Atkin, et al., Cancer Genet Cytogenet. 15:253–268 (1985).
Berger, et al., Cancer Genet Cytogenet 23:1–24 (1986).
Bittard, Michel., Bladder Cancer, Part A: Pathology, Diagnosis, and Surgery (Alan R. Liss, Inc., New York, NY)p. 161–176 (1984).
Blomjous, et al., A.J.C.P. 91:243–248 (1989).
Coombs, et al., Br. J. Cancer. 63:601–608 (1991).
Dalbagni, et al., The Lancet 342:469–471 (1993).
Gibas, et al., Cancer Res. 44:1257–1264 (1984).
Hopman, et al., American Journal of Pathology 135:1105–1116 (1989).
Hopman, et al., Modern Pathology 4:503–513 (1991).
Hopman, et al., Histochemistry 89:307–316 (1988).
Hopman, et al., Cancer Res. 51:644–651 (1991).
Koss, et al., Cancer 64:916–924 (1989).
Kurth, et al., Bladder Cancer Part A: Pathology, Diagnosis, and Surgery (Alan R. Liss, Inc., New York, NY)p. 307–318 (1984).
Limon, et al., Cancer Genet Cytogenet 23:305–313 (1986).
Murphy, et al., J. of Urology 136:815–819 (1986).
Nederof, et al., Cancer Genet Cytogenet 42:87–98 (1989).
Oncor, Inc. 1991 Annual Report, 4–5.
Oncor, Inc. 1992 Annual Report, 6–7.
Pinkel, et al., Proc. Natl. Acad. Sci. 83:2934–2938 (1986).
Poddighe, et al., Cancer Res. 52:4929–4934 (1992).
Presti, et al., Cancer Res. 51:5405–5409 (1991).
Sandberg, et al., Cancer Genet Cytogenet 19:163–175 (1986).
Sandberg, et al., J. Urol. 151:545–560 (1994).
Schapers, et al., Cancer Genet Cytogenet 70:56–61 (1993).
Sidransky, et al., Science 252:706–709 (1991).
Sidransky, et al., The New England Journal of Medicine 326:737–740 (1992).
Smeets, et al., Cancer Genet Cytogenet 29:29–41 (1987).
Smeets, et al., Int. J. Cancer 39:304–310 (1987).
Tsai, et al., Cancer Res. 50:44–47 (1990).
Waldman, et al., Cancer Res. 51:3807–3813 (1991).
Wang, et al., Cancer Genet Cytogenet 73:8–10 (1994).
Wright, et al., Br. J. Cancer 63:967–970 (1991).
Poddighe, et al., "Interphase Cytogenetics of Bladder Cancer", Cancer Res. 52(18), 1992, p. 4929–4934.*
Waldman et al., Cancer Res., 51(14), 1991, p. 3807–3813.*
Poddigh et al, Cancer Res. 52: 4929–4934 (1992).*
Waldman et al, Cancer Res. 51:3807–3813 (1991).*
Sandberg (Biosis Abstract) 16I : 76–9 (1992).*
Ford et al (Biosis Abstract) 43:733–740 (1988).*
Koss et al Acta Cytol 29(5):810–816 (1985).*

\* cited by examiner

*Primary Examiner*—Eggerton A. Campbell
(74) *Attorney, Agent, or Firm*—Glenn E. Karta; R. Thomas Gallegos (57) ABSTRACT

Cells collected from bladder washings or urine may be analyzed by in situ hybridization. Such analysis includes detection of bladder cancer or carcinoma-in-situ.

3 Claims, 5 Drawing Sheets

(5 of 5 Drawing Sheet(s) Filed in Color)

DETECTION OF BLADDER CANCER

This is a continuation of application Ser. No.08/330,239 filed Oct. 27, 1996 now abandoned which is a continuation of application Ser. No. 08/151,445 filed Nov. 12, 1993, now abandoned.

BACKGROUND OF THE INVENTION

1. Field of the Invention

The present invention relates to methods for the early detection of bladder cancer. In particular, bladder cancer is detected early by use of in situ hybridization of cells obtained from urine or bladder washings.

2. Description of Related Art

The publications and other materials used herein to illuminate the background of the invention and in particular cases to provide additional details respecting its practice are incorporated by reference and for convenience are numerically referenced in the following text and respectively grouped in the appended bibliography.

Cancer of the bladder is the fifth most common cancer in the United States with an annual incidence of about 18 cases per 100,000 or over 50,000 new cases per year, leading to more than 10,000 deaths annually. The incidence (80% of the cases) is highest in the 50–79 year age group; the disease prevalence peaks in the seventh decade of life with a strong male predominance. Bladder cancer accounts for 7% of all new cases of cancer among men and 3% among women, as well as 2% of cancer deaths among men and 1% among women. Occupational exposure may account for 21–25% of bladder cancer in white males in the United States.

Almost all cases of bladder cancer are of the transitional cell type (95%), and among those, approximately 80% appear initially as more or less well-differentiated, superficial papillary neoplasms with a tendency for multifocal or diffuse involvement of the urothelial surface and/or recurrent tumor episodes, but with limited potential for invasive growth.

Of special interest is carcinoma-in-situ (CIS) of the bladder, a lesion presenting problems in diagnosis and of unpredictable behavior (e.g. recurrence and progression) and where morphologic definition is arbitrary and generally defined as a total replacement of the urothelial surface by cells which bear morphologic features of the carcinoma, but which lack architectural alterations other than an increase in the number of cell layers, i.e., a flat lesion.

Cytogenetic analyses of bladder cancer have revealed recurrent abnormalities affecting several chromosomes, particularly structural rearrangements of chromosomes 5 and 9 and numerical changes of chromosome 7, 8, 9 and Y. Rearrangements of chromosomes 1, 10 and 11 have also been reported.

Recently, FISH has become the best alternative method to cytogenetic analysis of bladder cancer. Various studies have described numerical changes of chromosomes 7(+7), 8(+8), 9(−9) and Y(−Y) and less frequently 10 and 11.

Bladder cancer affects mostly elderly individuals with a male:female ratio of 5:1 and tends to recur often. Thus, consistent follow-up is imperative for these patients. Follow-up usually consists of cystoscopy, biopsy and x-ray examination. Some of those procedures, though necessary, are considered invasive methods, which are often uncomfortable for the patient. Bladder washings obtained during cystoscopy can be then analyzed histologically and for DNA content. However, that approach is not always successful, particularly when a limited number of cells is present in the sample. In particular, the structural changes i(5q),del(9q) have been often reported and among the numerical changes, −Y, +7, +8 and −9 were the most frequently observed. Unfortunately, cytogenetic results on bladder cancer are often difficult to obtain due to the poor growth of tumor cells in culture. In these cases, fluorescense in situ hybridization (FISH) has been used as an alternative technique in detecting numerical chromosome changes. To date, FISH has been performed on cultured cells and paraffin embedded tissue sections of bladder tumors with good results.

Sidransky, et al. [19] analysed tumor cells containing p53 gene mutations shed into the urine.

SUMMARY OF THE INVENTION

The present invention is based on the discovery that cells collected from urine or bladder washings may be analyzed by in situ hybridization techniques. One use of this discovery is that such cells may be analyzed to detect bladder cancer or carcinoma in situ. In one aspect, the present invention provides a method for detecting bladder cancer or carcinoma in situ, comprising the steps of:

a) performing in situ hybridization on cells obtained from the urine or bladder washing of a patient by contacting the cells under hybridization conditions with at least one detectable nucleic acid probe which will selectively hybridize to one chromosome in the cells;
  b) detecting the hybridized probe; and
  c) comparing the results in step b) to a predetermined in situ hybridization pattern obtained from normal cells, wherein the bladder cancer or carcinoma in situ is detected if the results obtained in step b) are different from the predetermined pattern.

The present invention is also directed to kits useful in the practice of the present methods.

BRIEF DESCRIPTION OF THE DRAWINGS

The claim of this patent contains at least one drawing executed in color.

FIGS. 1A–1D illustrates the signal pattern obtained using centromeric probes for chromosomes 7 and 8 according to the present invention. FIG. 1A shows the chromosome 7 probe. FIG. 1B shows the chromosome 8 probe.

DETAILED DESCRIPTION OF THE INVENTION

The cells to be analyzed according to the present method are obtained from either the urine or the bladder washings from a patient whose cells are desired to be analyzed. They are then subjected to in situ hybridization with nucleic acid probes suitable for the analysis in question. In a preferred embodiment of the present invention, the cells are analyzed to detect the presence of bladder cancer or carcinoma-in-situ. In that case, cells are obtained from a patient suspected of having, or to be tested for, those diseases. If the cells are to be obtained from urine, it is preferable to obtain them from the patient's first morning urine. A sufficient amount should be collected in order to obtain a suitable number of cells for analysis. A suitable amount is in the range of about 50 to about 100 ml of urine. If the cells are obtained from bladder washings, a suitable amount of washings to be collected is also in the range of about 50 to about 100 ml. The washing medium may be any liquid conventionally used, such as water and preferably saline solution.

The cells contained in the urine or bladder washings may be harvested in any suitable way. Preferably, the cells are harvested by centrifugation. Once the cells are harvested, they may be prepared for in situ hybridization by methods well known to one of ordinary skill. The cells may be analyzed within a short time after harvesting, or they may be fixed and stored for a longer period of time before analysis. The cells may be fixed by any suitable known fixative, such as ethanol or formalin. For in situ hybridization analysis, the cells are placed on a solid support suitable for examination by microscopy, such as a slide or coverslip, and treated by methods well known in the art to permeablize the cells so that detectable probe can enter the cells and bind to the chromosomal region.

The in situ hybridization of the present invention may be carried out in ways well known to the person skilled in the art. For example, a hybridization solution comprising at least one detectable nucleic acid probe capable of hybridizing to a chromosome within the cell is contacted with the cell under hybridization conditions. Any hybridization is then detected, then compared to a predetermined hybridization pattern from normal or control cells. It is preferred to use a nucleic acid probe which will selectively hybridize to only one chromosome. By selectively hybridize is meant that the probe will bind to a particular chromosome in an amount sufficient to detect the chromosome, without binding sufficiently to other chromosomes to allow identification of such other chromosomes. It is preferred that a probe be used that selectively binds to a chromosome that undergoes a numerical change in bladder cancer or carcinoma in situ. For example, one or more probes to chromosomes 1, 7, 8, 9, 10, 11, 17, Y and X may be used. Preferably, the probes are alpha-centromeric probes for the chromosomes listed above. Those probes are readily commercially available (Oncor, Inc., Gaithersburg, Md.). In a preferred embodiment, the hybridization solution contains a multiplicity of probes, each specific for a different chromosome. For example, the hybridization solution may contain an amount of a chromosome 7 probe and an amount of a chromosome 8 probe. Other possible combinations are apparent and within the scope of the present invention.

The probes may be prepared by any method known in the art, including synthetically or grown in a biological host. Synthetic methods include oligonucleotide synthesis, riboprobes, and PCR.

The probe may be labeled with a detectable marker by any method known in the art. Methods for labelling probes include random priming, end labeling, PCR and nick translation. Enzymatic labeling is conducted in the presence of nucleic acid polymerase, three unlabeled nucleotides, and a fourth nucleotide which is either directly labeled, contains a linker arm for attaching a label, or is attached to a hapten or other molecule to which a labeled binding molecule may bind. Suitable direct labels include radioactive labels such as $^{32}P$, $^{3}H$, and $^{35}S$ and non-radioactive labels such as fluorescent markers, such as fluorescein, Texas Red, AMCA blue, lucifer yellow, rhodamine, and the like; cyanin dyes which are detectable with visible light; enzymes and the like. Labels may also be incorporated chemically into DNA probes by bisulfite-mediated transamination or directly during oligonucleotide synthesis.

Specifically, fluorescent markers may be attached to nucleotides with activated linker arms which have been incorporated into the probe. Probes may be indirectly labeled by the methods disclosed above, by incorporating a nucleotide covalently linked to a hapten or other molecule such as biotin or digoxygenin, and performing a sandwich hybridization with a labeled antibody directed to that hapten or other molecule, or in the case of biotin, with avidin conjugated to a detectable label. Antibodies and avidin may be conjugated with a fluorescent marker, or with an enzymatic marker such as alkaline phosphatase or horseradish peroxidase to render them detectable. Conjugated avidin and antibodies are commercially available from companies such as Vector Laboratories (Burlingame, Calif.) and Boehringer Mannheim (Indianapolis, Ind.).

The enzyme can be detected through a calorimetric reaction by providing a substrate for the enzyme. In the presence of various substrates, different colors are produced by the reaction, and these colors can be visualized to separately detect multiple probes. Any substrate known in the art may be used. Preferred substrates for alkaline phosphatase include 5-bromo-4-chloro-3-indolylphosphate (BCIP) and nitro blue tetrazolium (NBT). The preferred substrate for horseradish peroxidase is diaminobenzoate (DAB).

Fluorescently labelled probes suitable for use in the in situ hybridization methods of the present invention are preferably in the range of 150–500 nucleotides long. Probes may be DNA or RNA, preferably DNA.

Hybridization of the detectable probes to the cells is conducted with a probe concentration of 0.1–500 ng/$\mu$l, preferably 5–250 ng/$\mu$l. The probe concentration is greater for a larger clone. The hybridization mixture will preferably contain a denaturing agent such as formamide. In general, hybridization is carried out at 25° C.–45° C., more preferably at 32° C.–40° C., and most preferably at 37° C.–38° C. The time required for hybridization is about 0.25–96 hours, more preferably 1–72 hours, and most preferably for 4–24 hours. Hybridization time will be varied based on probe concentration and hybridization solution content which may contain accelerators such as hnRNP binding protein, trialkyl ammonium salts, lactams, and the like. Slides are then washed with solutions containing a denaturing agent, such as formamide, and decreasing concentrations of sodium chloride or in any solution that removes unbound and mismatched probe.

The temperature and concentration of salt will vary depending on the stringency of hybridization which is desired. For example, high stringency washes may be carried out at 42° C.–68° C., while intermediate stringency may be in the range of 37° C.–55° C., and low stringency may be in the range of 30° C.–37° C. Salt concentration for a high stringency wash may be 0.5–1×SSC (0.15M NaCl, 0.015M Na citrate), while medium stringency may be 1×–4×, and low stringency may be 2×–6×SSC.

The detection incubation steps, if required, should preferably be carried out in a moist chamber at 23° C.–42° C., more preferably at 25° C.–38° C. and most preferably at 37°–38° C. Labeled reagents should preferably be diluted in a solution containing a blocking reagent, such as bovine serum albumin, non-fat dry milk, or the like. Dilutions may range from 1:10–1:10,000, more preferably 1:50–1:5,000, and most preferably at 1:100–1:1,000. The slides or other solid support should be washed between each incubation step to remove excess reagent.

Slides may then be mounted and analyzed by microscopy in the case of a visible detectable marker, or by exposure to autoradiographic film in the case of a radioactive marker. In the case of a fluorescent marker, slides are preferably mounted in a solution which contains an antifade reagent, and analyzed using a fluorescence microscope. Multiple nuclei may be examined for increased accuracy of detection.

The present invention is also directed to kits useful in the practice of the foregoing methods. Such kits will comprise at least one nucleic acid probe capable of selectively hybridizing to a chromosome to be analyzed. Preferably, the kit will contain one or more of a probe which will selectively hybridize to one of the following chromosomes: 1, 7, 8, 9, 10, 11, Y and X. The probe(s) may be contained within containers which are contained within a packaging material. The packaging material may contain a label which indicates that the contents may be used to detect bladder cancer or carcinoma-in-situ.

It will be recognized that the above descriptions are preferred methods of carrying out the process of the present invention and that numerous variations of the above methods can be made in the process following the teachings of this invention. The various process conditions can be altered and reagents used can be changed to provide various desired or optimum operating conditions for in situ hybridization.

The following examples are intended to further illustrate the invention and are not intended to limit the scope of the invention in any manner whatsoever.

EXAMPLE 1

FISH on Formalin-Fixed Cells from Bladder Washings

Slides were obtained on which cells from bladder washings were fixed by formalin. The slides were treated as follows:

1) pretreat in 20% $NaHSO_3$ for 10 minutes at 43° C. Wash slides with water, dehydrate in graded ethanol (1 minute each) then air dry.
2) Drop proteinase K (100 µg/ml in PBS) on slide, cover with a coverslip and incubate at 37° C. for 10–20 minutes. Wash with water, dehydrate in graded ethanol (1 minute each), then air dry.
3) denature slides in 70% formamide/2×SSC, pH 7.0 at 72° C. for 5 minutes, dehydrate in cold graded ethanol (2 minutes each).
4) denature probe mixture (1.5 µl of biotinylated centromeric probe (10 ng/ml; Oncor, Inc.) in 30 µl of Oncor Hybrisol®VI) at 75° C. for 5 minutes, then quench in ice.
5) hybridize probe and cells overnight at 37° C. in a humid chamber.
6) postwash slides in 65% formamide/2×SSC pH 7 for 12 minutes at 42° C., then 2×SSC for 8 minutes at 37° C.
7) develop signal with two layers of FITC-avidin, counterstain with propidium iodide in Oncor antifade solution.
8) detect signal. Any suitable system may be used, for example, an Olympus fluorescent microscope.

The results are shown below in Table 1, and clearly demonstrate that FISH analysis is possible on those cells.

TABLE 1

| | | Number of cells with 0, 1, 2, 3, 4 or 5 signals | | | | | | |
|---|---|---|---|---|---|---|---|---|
| Sample | Probe | 0 | 1 | 2 | 3 | 4 | 5 | no. cells |
| 1 | X | 22 | 24 | 5 | | | | 51 |
| 2 | X | | 45 | 51 | 8 | 3 | | 108 |
| 3 | X | | 39 | 55 | 2 | 4 | | 100 |
| 4 | X | | 96 | 4 | 1 | | 1 | 101 |
| 5 | X | | 5 | | | | | 5 |
| 5 | X | 6 | 43 | 16 | | 2 | | 67 |
| 6 | X | 6 | 27 | 4 | | 5 | | 42 |
| 7 | X | | 40 | 35 | 23 | 2 | | 100 |
| 8 | X | Bad background, not readable | | | | | | 20 |

Figure 6:
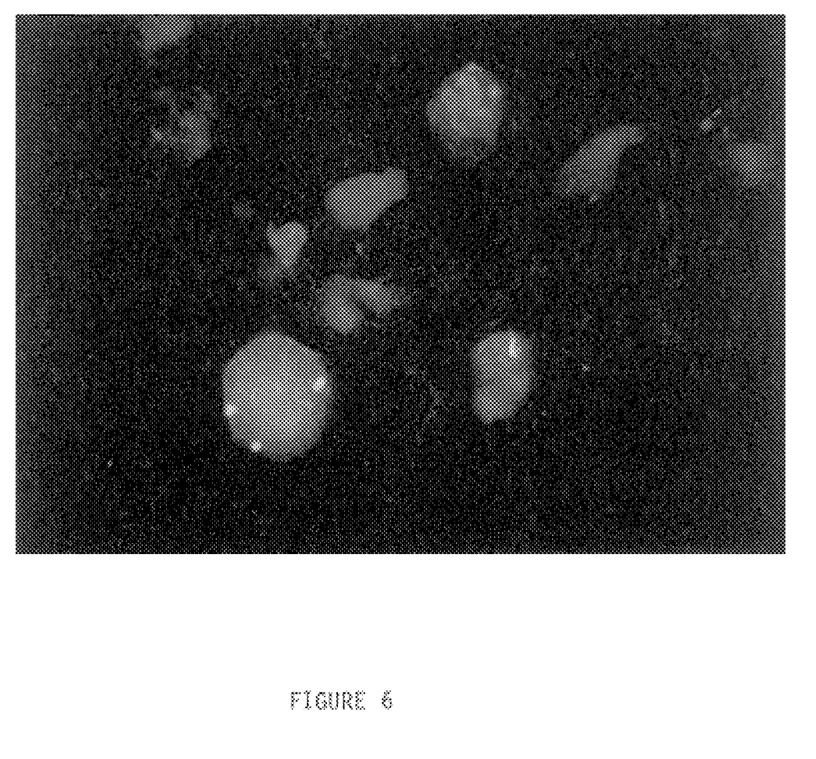
FIGS. 6 and 7 illustrate the signal pattern obtained using a centromeric probe for chromosome X in cells obtained from bladder washing.

FIG. 6 illustrates the signal pattern obtained from cells analyzed according to Example 1. Three discrete signals are clearly seen in the lower-left cell, indicating trisomy X.

EXAMPLE 2

Analysis of Ethanol Fixed Cells

The following protocol may be used to analyze cells isolated from bladder washings which have been fixed in ethanol:

1) wash cells twice in PBS with 5 mM EDTA. Spin at 1000 RPM for 10 minutes.
2) add 2 ml of Hematall (Fisher Diagnostics, Orangeburg, N.Y.) to the cell pellet, mix evenly and incubate at 0° C. for 15 minutes.
3) add PBS with 5 mM EDTA to make more than 10 ml, mix then spin down cells at 1500 RPM for 10 minutes.
4) repeat step 3).
5) add 2 ml proteinase K, 100 mg/ml in PBS to the cell pellet, mix evenly, incubate at 37° C. for 15 minutes.
6) add methanol:acetic acid (3:1) drop by drop while shaking the cell suspension violently (by habd or on a vortex), to 12 ml.
7) spin down (1500 RPM for 10 minutes), remove supernatant, add fresh methanol:acetic acid (3:1) to form a cell suspension.
8) make slides by dropping cell suspension on regular slides; air dry.
9) denature slides in 70% formamide/2×SSC, pH 7.0 at 72° C. for 5 minutes, dehydrate in cold graded ethanol (2 minutes each), air dry.
10) denature probe mixture (1 µl of biotinylated centromeric probe (Oncor, Inc.) in 30 µl of Oncor Hybrisol®VI) at 75° C. for 5 minutes, then quench in ice.
11) hybridize probe and cells overnight at 37° C. in a humid chamber.
12) postwash slides in 65% formamide/2×SSC pH 7 for 12 minutes at 42° C., then 2×SSC for 8 minutes at 37° C.
13) develop signal with two layers of FITC-avidin, counterstain with propidium iodide in Oncor antifade solution.
14) detect signal. Any suitable system may be used, for example, an Olympus fluorescent microscope.

Figure 7:
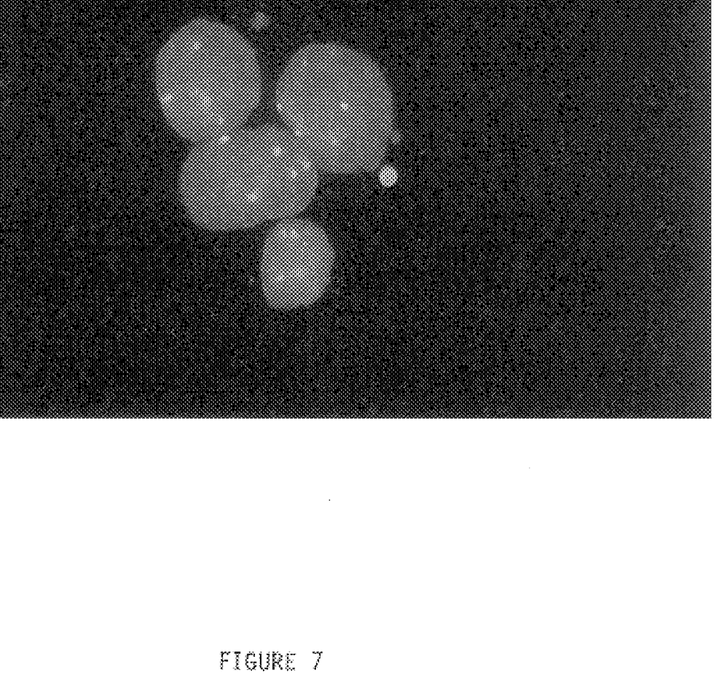

FIG. 7 illustrates the signal pattern obtained from cells analyzed according to Example 2. Five discrete signals are clearly seen in the cell in the middle of the line of three cells, indicating pentasomy X.

EXAMPLE 3

Control Patients

Forty five human individuals (39 males and 6 females) without bladder cancer were used as controls in this Example. Samples of urine and bladder washings were collected from each individual, and FISH analyses were performed as follows.

In the case of urine analysis, samples were collected (at least 50 ml) usually in the morning. In the case of bladder washings, 50 to 100 ml were obtained, performed if possible with saline solution, during cystoscopy or prior to surgery. Cells from the samples were harvested according to the following protocol:

1) spin the samples at 1200 rpm in a table top centrifuge for 6–8 minutes.
2) discard the supernatent and resuspend the pellet with 8–10 ml of phosphate-buffered saline (PBS). Combine pellets of same sample and transfer to 15 ml centrifuge tube.
3) centrifuge as in 1).
4) aspirate the supernatant and add 5–10 ml of pre-warmed (37° C.) 0.075 KCl hypotonic solution. Let sit at room temperature for ten minutes.
5) add a few drops of fixative (methanol-acetic acid 3:1). Centrifuge as in 1).
6) Aspirate supernatent and add 5–10 ml of fixative. Let sit at room temperature for 20 minutes.
7) Repeat 1) and 6) twice using 10 ml of fixative.
8) Make slides immediately or store at 4° C. in the last fixative until slides are made.

After preparation, slides were made by centrifuging the fixed suspension at 1200 rpm for 6–8 minutes. The supernatent was aspirated, followed by resuspension with 40 µl of fresh fixative. Twenty µl of suspension were dropped on a slide, followed immediately by a few drops of 65% acetic acid in distilled water. The slides were allowed to sit for a few seconds, then tilted and air dried flat. They were then stored in 70% ethanol at 4° C. until ready to be processed with FISH.

Hybridization was performed following a modified version of the technique described by Pinkel, et al. [10]. Slides were denatured in 70% formamide/2×SSC, pH7, at 70° C. for two minutes, then dehydrated in an ice cold ethanol series. The hybridization mixture consisted of 55% formamide, 10% dextran sulfate, 50 µg/ml carrier DNA and 80 ng/ml probe DNA. The mixture was denatured for 5 minutes at 70° C. and applied to pre-warmed (37° C.) slides under a coverslip at a volume of 0.02 µl per cm$^2$. Slides were sealed with rubber cement and hybridized overnight (16–22 hours) at 37° C. in a moist chamber.

The DNA probes used were alpha-satellite probes for chromosomes 7, 8, 9 (classical), 10, 11, Y (for males) and X (for females). All of the probes were supplied by and are commercially available from Oncor, Inc of Gaithersburg, Md.

Post hybridization washes were performed in 50% formamide, 2×SSC, pH 7.0, followed by successive washes at room temperature in 2×SSC, pH 7.0 and PN buffer (0.1M NaPO$_4$, pH 8.0, 0.1% NP-40). The hybridized probe was detected by fluorescein-avidin DCS (Vector Laboratories, Burlingame, Calif.) at a final concentration of 5 µg/ml in PNM buffer (PN buffer with 5% non-fat milk and 0.2% NaN$_3$). Amplification was carried out by using biotinylated goat antiavidin (Vector) at a concentration of 5 µg/ml in PNM buffer, followed by another layer of fluorescein-avidin. Nuclei were counterstained with an antifade solution containing propidium iodide (1 µg/ml).

Twelve of these control individuals had successful FISH results, and nine of these were used to create a chart of control values. The normal values for probes of chromosomes 7, 8, 9, 10, 11 and Y are presented below, together with their standard deviations calculated on the basis of n=9. Probe X was not included because none of the six female control samples yielded FISH results.

Table 1 presents the FISH results in connection with cells collected from urine. Table 2 presents the FISH results in connection with cells collected from bladder washings. In each Table, the results for each probe are based on analysis of 100 cells.

TABLE 2

Urine
Number of cells with 0, 1, 2, 3, or 4 signals

| Probe | 0 | 1 | 2 | 3 | 4 |
|---|---|---|---|---|---|
| Y | 3.1 ± 1.3 | 95.3 ± 2.0 | 1.3 ± 1.5 | 0.1 ± 0.3 | 0 |
| 9 | 0 | 5 ± 1.8 | 92.6 ± 3.9 | 1.8 ± 2.4 | 0.3 ± 0.7 |
| 8 | 0.2 ± 0.6 | 3.2 ± 1.5 | 93.8 ± 3.3 | 1.2 ± 1.6 | 0 |
| 10 | 0.2 ± 0.6 | 3.7 ± 2.4 | 95.6 ± 3.0 | 0.6 ± 0.9 | 0 |
| 7 | 0.2 ± 0.4 | 6.7 ± 1.6 | 91.9 ± 2.4 | 1 ± 2.5 | 0.2 ± 0.6 |
| 11 | 0 | 6.9 ± 2.5 | 93.2 ± 2.1 | 0.1 ± 0.3 | 0.2 ± 0.4 |

TABLE 3

Bladder washings
Number of cells with 0, 1, 2, 3, or 4 signals

| Probe | 0 | 1 | 2 | 3 | 4 |
|---|---|---|---|---|---|
| Y | 4.6 ± 2.5 | 94.2 ± 3.0 | 1.7 ± 1.6 | 0 | 0 |
| 9 | 0.3 ± 0.7 | 4.3 ± 1.4 | 94.7 ± 1.8 | 0.3 ± 0.7 | 0.2 ± 0.6 |
| 8 | 0.1 ± 0.3 | 3.3 ± 2.6 | 96.2 ± 3.0 | 0.3 ± 0.7 | 0 |
| 10 | 0.6 ± 1.3 | 3.3 ± 2.6 | 95.6 ± 3.4 | 0.6 ± 0.8 | 0 |
| 7 | 0.2 ± 0.6 | 6 ± 2.1 | 93.1 ± 2.5 | 0.6 ± 0.7 | 0 |
| 11 | 0 | 6.3 ± 3.5 | 92.6 ± 2.4 | 1 ± 0.3 | 0 |

EXAMPLE 4

FISH analysis was performed on urine samples and/or bladder washings (as in Example 3) and/or tumor tissue from 23 human patients (21 males, 2 females; patients 4 and 28 were female). Table 4 presents the results. In the table, "U" represents a urine sample, "BW" represents a bladder washing sample, and "TT" represents tumor tissue. Patients 1, 2, 4, 13, 15, 17, 25 and 28 were diagnosed with bladder cancer. Patient 5 was diagnosed with carcinoma-in-situ. Patients 6, 10, 14, 22, 24, and 29 had a history of bladder cancer without recurrences, and Patients 8, 12, 18, 23, 27 and 30–32 had a history of recurrent bladder cancer. Patient 4 had two tumors, left ("L") and right ("R") which were analyzed. Patient 8 had two urine samples analyzed and patients 5 and 8 had two bladder washings analyzed. Further, some of the tumor samples were subjected to standard cytogenetic analyses, the results of which are also set forth in the table. Certain probes were not used in connection with certain samples; those are indicated by "*".

TABLE 4

Percent of cells with 0, 1, 2, 3, 4 or >4 signals

| Patient | Probe | 0 | 1 | 2 | 3 | 4 | >4 | no. cells |
|---|---|---|---|---|---|---|---|---|
| 1 U | Y |  | 33 | 65 | 2 |  |  | 100 |
|  | 7 |  | 1 | 30 | 34 | 15 |  | 100 |
|  | 8 |  |  | 37 | 53 | 10 |  | 100 |
|  | 9 | 1 | 8 | 78 | 13 |  |  | 100 |
|  | 10 |  |  | 32 | 45 | 20 | 3 | 93 |
|  | 11 |  | 3 | 67 | 23 | 7 |  | 100 |
| 1 BW | Y | 2 | 38 | 60 |  |  |  | 100 |
|  | 7 |  | 3 | 49 | 44 | 4 |  | 100 |
|  | 8 |  |  | 30 | 70 |  |  | 100 |
|  | 9 |  | 9 | 73 | 18 |  |  | 100 |
|  | 10 |  |  | 33 | 53 | 13 |  | 75 |
|  | 11 |  | 3 | 70 | 25 | 2 |  | 100 |
| 1 TT | Y | 1 | 54 | 45 |  |  |  | 100 |
|  | 7 |  | 3 | 71 | 14 | 12 |  | 100 |
|  | 8 |  | 2 | 29 | 54 | 15 |  | 100 |
|  | 9 | 1 | 17 | 73 | 9 |  |  | 100 |
|  | 10 |  | 6 | 69 | 15 | 10 |  | 100 |
|  | 11 |  | 5 | 87 | 7 | 1 |  | 100 |
| 2 U | Y | 1 | 96 | 3 |  |  |  | 100 |
|  | 7 |  | 5 | 92 | 1 |  | 2 |  | 100 |
|  | 8 |  | 4 | 94 |  | 2 |  | 100 |
|  | 9 |  | 4 | 96 |  |  |  | 100 |
|  | 10 |  | 3 | 97 |  |  |  | 100 |
|  | 11 |  | 8 | 90 | 1 | 1 |  | 100 |
| 2 BW | Y |  | 90 | 10 |  |  |  | 100 |
|  | 7 |  | 2 | 96 |  | 2 |  | 100 |
|  | 8 |  | 1 | 95 | 2 | 2 |  | 100 |
|  | 9 |  | 5 | 94 | 1 |  |  | 100 |
|  | 10 |  | 5 | 94 | 1 |  |  | 100 |
|  | 11 |  | 7 | 90 |  | 3 |  | 100 |
| 2 TT | Y | 2 | 95 | 3 |  |  |  | 100 |
|  | 7 |  | 6 | 90 | 3 | 1 |  | 100 |
|  | 8 |  | 2 | 95 | 1 | 2 |  | 100 |
|  | 9 |  | 6 | 92 | 2 |  |  | 100 |
|  | 10 |  | 9 | 86 | 3 | 2 |  | 100 |
|  | 11 | 1 | 9 | 86 | 1 | 3 |  | 100 |
|  | Cytogenetics: 46, XY | | | | | | | |
| 4 U | X | 1 | 3 | 92 | 4 |  |  | 100 |
|  | 7 |  | 3 | 90 | 5 | 2 |  | 100 |
|  | 8 |  |  | 57 | 39 | 2 | 2 | 100 |
|  | 9 |  | 9 | 90 | 1 |  |  | 100 |
|  | 10 |  | 4 | 92 | 1 | 1 | 2 | 100 |
|  | 11 |  | 6 | 92 | 1 | 1 |  | 100 |
|  | 1 |  | 5 | 95 |  |  |  | 22 |
|  | 17 |  | 5 | 92 |  | 3 |  | 38 |
| 4 BW | X |  | 2 | 84 | 12 | 2 | 1 | 100 |
|  | 7 |  | 4 | 77 | 10 | 6 | 3 | 95 |
|  | 8 |  |  | 39 | 54 | 2 | 5 | 100 |
|  | 9 |  | 6 | 90 | 3 | 1 |  | 100 |
|  | 10 |  | 3 | 88 | 3 | 3 | 3 | 37 |
|  | 11 |  | 9 | 84 | 7 |  |  | 96 |
|  | 1 |  | 5 | 95 |  |  |  | 21 |
|  | 17 |  | 7 | 93 |  |  |  | 27 |
| 4 TT (L) | X |  |  | 72 | 28 |  |  | 100 |
|  | 7 |  |  | 33 | 21 | 22 | 24 | 100 |
|  | 8 |  |  | 62 | 38 |  |  | 100 |
|  | 9 | 1 | 9 | 90 |  |  |  | 100 |
|  | 10 |  | 6 | 94 |  |  |  | 100 |
|  | 11 |  | 2 | 64 | 22 | 12 |  | 100 |
|  | 1 |  |  | 87 | 3 | 10 |  | 40 |
|  | 17 |  | 5 | 51 | 34 |  |  | 100 |
|  | Cytogenetics: 46, xx | | | | | | | |
| 4 TT (R) | X |  |  | 37 | 63 |  |  | 100 |
|  | 7 |  | 7 | 92 |  | 1 |  | 100 |
|  | 8 |  | 3 | 52 | 45 |  |  | 100 |
|  | 9 |  | 2 | 97 | 1 |  |  | 100 |
|  | 10 |  | 3 | 97 |  |  |  | 100 |
|  | 11 |  | 10 | 90 | 1 |  |  | 100 |
|  | 1 |  | 4 | 93 | 2 | 1 |  | 100 |
|  | 17 |  | 9 | 91 |  |  |  | 100 |
|  | Cytogenetics: 47, X, der(X), +der(8), del(9p), −19, +mar[cx] | | | | | | | |
| 5 U | Y |  | 8 | 92 |  |  |  | 100 |
|  | 7 |  |  | 7 | 84 | 6 | 3 | 100 |
|  | 8 |  |  | 3 | 88 | 9 |  | 100 |
|  | 9 |  |  | 6 | 94 |  |  | 100 |
|  | 10 |  | 2 | 12 | 79 | 6 | 1 | 100 |
|  | 11 |  |  | 8 | 82 | 9 |  | 100 |
| 5 BW (1st) | Y | * |  |  |  |  |  |  |
|  | 7 |  |  | 6 | 88 | 4 | 2 | 68 |
|  | 8 |  |  | 1 | 91 | 8 |  | 87 |
|  | 9 |  |  | 2 | 98 |  |  | 45 |
|  | 10 |  | 1 | 5 | 91 | 2 | 1 | 88 |
|  | 11 |  |  | 2 | 92 | 6 |  | 47 |
| 5 BW (2nd) | Y | 14 | 84 | 2 |  |  |  | 100 |
|  | 7 |  |  | 7 | 84 | 6 | 3 | 100 |
|  | 8 |  |  | 3 | 88 | 9 |  | 100 |
|  | 9 |  |  | 7 | 88 |  | 5 | 100 |
|  | 10 |  | 1 | 17 | 78 | 4 |  | 100 |
|  | 11 | 1 | 1 | 12 | 80 | 5 | 2 | 100 |
| 6 U | Y | 3 | 97 |  |  |  |  | 100 |
|  | 7 |  |  | 5 | 95 |  |  | 100 |
|  | 8 |  |  | 3 | 96 |  |  | 100 |
|  | 9 |  |  | 7 | 93 |  |  | 100 |
|  | 10 |  |  | 7 | 93 |  |  | 100 |
|  | 11 |  |  | 6 | 94 |  |  | 100 |
| 6 BW | Y | 3 | 97 |  |  |  |  | 63 |
|  | 7 |  |  | 4 | 96 |  |  | 100 |
|  | 8 |  |  | 2 | 97 | 1 |  | 100 |
|  | 9 |  |  | 4 | 96 |  |  | 57 |
|  | 10 |  |  | 3 | 97 |  |  | 87 |
|  | 11 |  |  | 8 | 92 |  |  | 100 |
| 8 U (1st) | Y | 5 | 89 | 6 |  |  |  | 80 |
|  | 7 |  |  | 7 | 66 | 18 | 9 | 100 |
|  | 8 | 1 | 3 | 42 | 46 | 8 |  | 100 |
|  | 9 | 2 | 2 | 77 | 17 | 2 |  | 95 |
|  | 10 | 2 | 7 | 82 | 7 | 2 |  | 100 |
|  | 11 | 2 | 5 | 65 | 17 | 11 |  | 100 |
| 8 BW (1st) | Y | 8 | 86 | 6 |  |  |  | 100 |
|  | 7 |  | 3 | 62 | 26 | 9 |  | 100 |
|  | 8 |  | 2 | 54 | 31 | 15 |  | 100 |
|  | 9 |  |  | 66 | 32 | 2 |  | 100 |
|  | 10 | 2 | 12 | 67 | 16 | 3 |  | 100 |
|  | 11 | 1 | 2 | 63 | 27 | 7 |  | 100 |
| 8 U (2nd) | Y | 2 | 83 | 15 |  |  |  | 52 |
|  | 7 |  |  | 43 | 51 | 6 |  | 37 |
|  | 8 |  |  | 65 | 27 | 8 |  | 82 |
|  | 9 |  | 2 | 66 | 30 | 2 |  | 100 |
|  | 10 |  |  | 55 | 25 |  |  | 100 |
|  | 11 |  | 1 | 62 | 26 | 11 |  | 85 |
| 8 BW (2nd) | Y | 2 | 73 | 25 |  |  |  | 40 |
|  | 7 |  |  | 59 | 25 | 3 |  | 100 |
|  | 8 |  | 5 | 71 | 20 | 4 |  | 100 |
|  | 9 |  |  | 62 | 30 | 8 |  | 100 |
|  | 10 |  | 1 | 51 | 25 | 3 |  | 100 |
|  | 11 |  | 2 | 74 | 21 | 3 |  | 100 |
| 10 U | Y | 23 | 69 | 8 |  |  |  | 100 |
|  | 7 | 6 | 9 | 80 |  | 3 |  | 100 |
|  | 8 | 2 | 2 | 92 |  | 3 |  | 100 |
|  | 9 |  | 3 | 94 |  | 3 |  | 70 |
|  | 10 | 1 | 3 | 90 |  | 4 |  | 100 |
|  | 11 | 2 | 8 | 88 |  | 2 |  | 50 |
| 10 BW | Y | 47 | 50 | 3 |  |  |  | 60 |
|  | 7 |  | 1 | 94 | 1 | 4 |  | 100 |
|  | 8 |  | 1 | 91 | 2 | 6 |  | 100 |
|  | 9 | 4 | 2 | 90 |  | 4 |  | 100 |
|  | 10 | 4 | 4 | 90 |  | 2 |  | 100 |
|  | 11 |  | 4 | 95 |  | 1 |  | 100 |
| 12 U | Y |  | 44 | 25 | 26 | 5 |  | 100 |
|  | 7 |  |  | 40 | 18 | 18 | 24 | 100 |
|  | 8 |  |  | 26 | 14 | 22 | 38 | 100 |
|  | 9 |  | 6 | 44 | 30 | 15 | 5 | 54 |
|  | 10 |  | 9 | 30 | 16 | 55 |  | 79 |
|  | 11 |  | 6 | 15 | 31 | 16 | 32 | 61 |

TABLE 4-continued

Percent of cells with 0, 1, 2, 3, 4 or >4 signals

| Patient | Probe | 0 | 1 | 2 | 3 | 4 | >4 | no. cells |
|---|---|---|---|---|---|---|---|---|
| 12 TT | Y | 1 | 93 | 6 |  |  |  | 71 |
|  | 7 |  |  | 86 | 4 | 10 |  | 100 |
|  | 8 |  |  | 17 | 53 | 6 | 14 | 100 |
|  | 9 |  | 5 | 83 | 1 | 11 |  | 96 |
|  | 10 |  | 1 | 16 | 64 | 9 | 10 | 86 |
|  | 11 |  |  | 7 | 83 | 10 |  | 75 |
| 13 U | Y | 1 | 62 | 36 | 1 |  |  | 100 |
|  | 7 |  |  | 69 | 25 | 6 |  | 100 |
|  | 8 |  |  | 52 | 22 | 16 | 10 | 100 |
|  | 9 |  | 2 | 96 | 2 |  |  | 100 |
|  | 10 |  |  | 71 | 18 | 7 | 4 | 100 |
|  | 11 |  | 2 | 95 | 3 |  |  | 100 |
| 13 BW | Y | 4 | 10 | 74 | 11 | 1 |  | 100 |
|  | 7 |  |  | 9 | 60 | 18 | 13 | 100 |
|  | 8 |  |  | 1 | 51 | 16 | 32 | 100 |
|  | 9 |  | 5 | 92 | 1 | 2 |  | 100 |
|  | 10 |  |  | 2 | 35 | 47 | 16 | 100 |
|  | 11 |  | 2 | 71 | 15 | 12 |  | 100 |
| 13 TT | Y | 2 | 15 | 80 | 3 |  |  | 100 |
|  | 7 |  | 2 | 44 | 53 |  | 1 | 100 |
|  | 8 |  |  | 14 | 54 | 16 | 16 | 100 |
|  | 9 |  | 4 | 96 |  |  |  | 100 |
|  | 10 |  |  | 31 | 59 |  | 10 | 81 |
|  | 11 |  | 11 | 87 | 22 |  |  | 100 |
| 14 U | Y | 2 | 90 | 6 | 2 |  |  | 100 |
|  | 7 |  | 7 | 92 | 1 |  |  | 100 |
|  | 8 |  | 2 | 97 | 1 |  |  | 100 |
|  | 9 | 1 | 7 | 88 | 4 |  |  | 100 |
|  | 10 |  | 3 | 97 |  |  |  | 100 |
|  | 11 |  | 9 | 91 |  |  |  | 100 |
| 14 BW | Y | 8 | 88 | 4 |  |  |  | 25 |
|  | 7 |  | 4 | 93 | 3 |  |  | 45 |
|  | 8 | 5 | 5 | 90 |  |  |  | 22 |
|  | 9 |  | 6 | 93 | 1 |  |  | 52 |
|  | 10 | 3 | 3 | 91 | 3 |  |  | 29 |
|  | 11 |  | 6 | 94 |  |  |  | 50 |
| 15 BW | Y |  | 69 | 29 | 2 |  |  | 100 |
|  | 7 |  | 56 | 44 |  |  |  | 100 |
|  | 8 |  |  | 98 | 2 |  |  | 100 |
|  | 9 |  | 94 | 6 |  |  |  | 100 |
|  | 10 |  | 2 | 98 |  |  |  | 100 |
|  | 11 |  | 7 | 93 |  |  |  | 100 |
| 15 TT | Y | 2 | 87 | 11 |  |  |  | 87 |
|  | 7 |  | 6 | 94 |  |  |  | 100 |
|  | 8 |  | 4 | 95 | 1 |  |  | 100 |
|  | 9 | 3 | 59 | 38 |  |  |  | 65 |
|  | 10 | 2 | 74 | 24 |  |  |  | 71 |
|  | 11 | 1 | 6 | 93 |  |  |  | 100 |
|  | 1 |  | 4 | 96 |  |  |  | 23 |
|  | 17 |  | 6 | 94 |  | 3 |  | 54 |
| Cytogenetics: 44–45, add(Xp), −Y, del(7q), der(9), t(9;?) (?q10;?), der(7;10), (?;?p10), −11, +4mar[cx] ||||||||
| 17 U | Y | 2 | 96 | 2 |  |  |  | 100 |
|  | 7 |  | 6 | 92 |  | 2 |  | 100 |
|  | 8 |  | 5 | 94 |  | 1 |  | 100 |
|  | 9 |  | 4 | 91 | 2 | 3 |  | 100 |
|  | 10 |  | 5 | 95 |  |  |  | 100 |
|  | 11 |  | 7 | 88 | 1 | 4 |  | 100 |
| 17 BW | Y | 1 | 96 | 3 |  |  |  | 100 |
|  | 7 |  | 2 | 96 |  | 2 |  | 100 |
|  | 8 |  | 2 | 97 | 1 |  |  | 100 |
|  | 9 |  | 5 | 95 |  |  |  | 100 |
|  | 10 |  | 2 | 97 |  | 1 |  | 100 |
|  | 11 |  | 1 | 98 |  | 1 |  | 100 |
| 17 TT | Y | 3 | 93 | 3 | 1 |  |  | 100 |
|  | 7 |  | 1 | 96 | 1 | 2 |  | 100 |
|  | 8 |  | 2 | 97 |  | 1 |  | 100 |
|  | 9 |  | 3 | 95 | 2 |  |  | 100 |
|  | 10 |  |  | 96 | 1 | 3 |  | 100 |
|  | 11 |  | 5 | 95 |  |  |  | 100 |
| 18 U | Y |  | 87 | 13 |  |  |  | 70 |
|  | 7 |  |  | 91 | 7 | 2 |  | 44 |
|  | 8 |  |  | 92 | 8 |  |  | 78 |
|  | 9 |  | 3 | 96 | 1 |  |  | 73 |
|  | 10 |  |  | 98 | 2 |  |  | 51 |
|  | 11 |  | 4 | 88 |  | 6 |  | 48 |
| 18 BW | Y |  | 81 | 15 | 4 |  |  | 100 |
|  | 7 |  | 2 | 86 | 12 |  |  | 100 |
|  | 8 |  |  | 76 | 15 | 9 |  | 96 |
|  | 9 |  | 5 | 92 | 3 |  |  | 100 |
|  | 10 |  | 3 | 90 | 7 |  |  | 100 |
|  | 11 | 2 | 6 | 92 |  |  |  | 50 |
| 22 U | Y | 3 | 97 |  |  |  |  | 65 |
|  | 7 |  | 7 | 92 | 1 |  |  | 100 |
|  | 8 |  | 4 | 96 |  |  |  | 100 |
|  | 9 |  | 7 | 93 |  |  |  | 44 |
|  | 10 |  | 4 | 96 |  |  |  | 26 |
|  | 11 |  | 10 | 90 |  |  |  | 57 |
| 22 BW | Y | 5 | 93 | 2 |  |  |  | 100 |
|  | 7 |  | 10 | 90 |  |  |  | 100 |
|  | 8 |  | 2 | 98 |  |  |  | 100 |
|  | 9 |  | 6 | 93 | 1 |  |  | 70 |
|  | 10 |  | 10 | 90 |  |  |  | 100 |
|  | 11 |  | 8 | 92 |  |  |  | 90 |
| 23 U | Y | 3 | 96 | 1 |  |  |  | 100 |
|  | 7 |  | 4 | 96 |  |  |  | 100 |
|  | 8 |  | 1 | 98 |  | 1 |  | 100 |
|  | 9 |  | 8 | 91 |  | 1 |  | 100 |
|  | 10 |  | 9 | 91 |  |  |  | 100 |
|  | 11 |  | 8 | 92 |  |  |  | 93 |
| 23 BW | Y | 2 | 98 |  |  |  |  | 100 |
|  | 7 |  | 1 | 99 |  |  |  | 100 |
|  | 8 |  | 6 | 94 |  |  |  | 53 |
|  | 9 |  | 7 | 93 |  |  |  | 84 |
|  | 10 |  | 6 | 94 |  |  |  | 80 |
|  | 11 |  | 6 | 94 |  |  |  | 100 |
| 24 U | Y | 4 | 94 | 2 |  |  |  | 100 |
|  | 7 | 2 | 10 | 88 |  |  |  | 100 |
|  | 8 | 1 | 7 | 92 |  |  |  | 100 |
|  | 9 |  | 2 | 98 |  |  |  | 100 |
|  | 10 | 1 | 6 | 92 | 1 |  |  | 100 |
|  | 11 |  | 8 | 92 |  |  |  | 100 |
| 24 BW | Y | 2 | 96 | 2 |  |  |  | 100 |
|  | 7 | 1 | 7 | 92 |  |  |  | 100 |
|  | 8 | 2 | 6 | 92 |  |  |  | 100 |
|  | 9 |  | 4 | 96 |  |  |  | 100 |
|  | 10 | 2 | 8 | 90 |  |  |  | 100 |
|  | 11 |  | 10 | 90 |  |  |  | 51 |
| 25 U | Y | 1 | 99 |  |  |  |  | 100 |
|  | 7 |  | 4 | 83 | 13 |  |  | 100 |
|  | 8 |  | 2 | 86 | 12 |  |  | 100 |
|  | 9 | * |  |  |  |  |  |  |
|  | 10 |  | 7 | 93 |  |  |  | 100 |
|  | 11 |  | 8 | 82 | 10 |  |  | 100 |
|  | 1 |  | 5 | 89 | 3 | 3 |  | 100 |
|  | 17 | 2 | 17 | 80 |  | 1 |  | 100 |
| 25 BW | Y |  | 94 | 6 |  |  |  | 100 |
|  | 7 |  | 1 | 69 | 18 | 12 |  | 100 |
|  | 8 |  |  | 71 | 14 | 15 |  | 100 |
|  | 9 |  | 7 | 93 |  |  |  | 100 |
|  | 10 |  | 5 | 95 |  |  |  | 100 |
|  | 11 |  | 7 | 71 | 16 | 6 |  | 100 |
| 25 TT | Y | 2 | 98 |  |  |  |  | 48 |
|  | 7 |  |  | 42 | 27 | 8 | 23 | 74 |
|  | 8 |  | 1 | 68 | 16 | 15 |  | 100 |
|  | 9 |  | 4 | 92 |  | 4 |  | 55 |
|  | 10 |  | 5 | 83 | 7 | 5 |  | 59 |
|  | 11 |  | 4 | 62 | 17 | 13 | 4 | 53 |
|  | 1 |  | 3 | 80 | 11 | 4 | 2 | 100 |
|  | 17 |  | 11 | 80 | 5 | 2 | 2 | 100 |

TABLE 4-continued

Percent of cells with 0, 1, 2, 3, 4 or >4 signals

| Patient | Probe | 0 | 1 | 2 | 3 | 4 | >4 | no. cells |
|---|---|---|---|---|---|---|---|---|
| Cytogenetics: 46, XY | | | | | | | | |
| 27 TT | Y | 88 | 12 | | | | | 100 |
| | 7 | | 11 | 89 | | | | 100 |
| | 8 | | 2 | 78 | 20 | | | 100 |
| | 9 | | 8 | 92 | | | | 62 |
| | 10 | | 10 | 90 | | | | 49 |
| | 11 | | 14 | 86 | | | | 44 |
| | 1 | | 6 | 94 | | | | 16 |
| | 17 | | 14 | 81 | 5 | | | 43 |
| Cytogenetics: 45–46, −Y, −8, +der(8p)x2, del(10q), add(11p), +2mar [cx] | | | | | | | | |
| 28 U | X | * | | | | | | |
| | 7 | | 7 | 91 | 2 | | | 82 |
| | 8 | | 3 | 88 | 7 | 2 | | 93 |
| | 9 | | 3 | 96 | 1 | | | 100 |
| | 10 | | 2 | 96 | 2 | | | 100 |
| | 11 | | 4 | 94 | 2 | | | 51 |
| 28 BW | X | * | | | | | | |
| | 7 | | 6 | 89 | 3 | 2 | | 100 |
| | 8 | | 2 | 92 | 4 | 2 | | 100 |
| | 9 | * | | | | | | |
| | 10 | | 1 | 97 | 1 | 1 | | 100 |
| | 11 | 1 | 4 | 91 | 3 | 1 | | 100 |
| | 1 | | 9 | 91 | | | | 23 |
| | 17 | | 13 | 87 | | | | 41 |
| 28 TT | X | * | | | | | | |
| | 7 | | 2 | 65 | 32 | 1 | | 100 |
| | 8 | | | 55 | 45 | | | 100 |
| | 9 | | 1 | 78 | 13 | 8 | | 100 |
| | 10 | | 2 | 82 | 10 | 6 | | 100 |
| | 11 | | 1 | 63 | 24 | 12 | | 100 |
| | 1 | | 6 | 89 | 3 | 2 | | 100 |
| | 17 | | 10 | 88 | 2 | | | 100 |
| Cytogenetics: 63–69, XXX, +der(7q), +der(11q)x2, +10mar[cx] | | | | | | | | |
| 29 BW | Y | 3 | 66 | 31 | | | | 39 |
| | 7 | | 5 | 95 | | | | 20 |
| | 8 | | | 14 | 82 | 4 | | 100 |
| | 9 | 3 | | 97 | | | | 35 |
| | 10 | | 5 | 95 | | | | 40 |
| | 11 | | 5 | 95 | | | | 65 |
| 30 BW | Y | 4 | 96 | | | | | 83 |
| | 7 | | 6 | 94 | | | | 100 |
| | 8 | | 3 | 97 | | | | 100 |
| | 9 | | 5 | 95 | | | | 100 |
| | 10 | | 5 | 95 | | | | 100 |
| | 11 | | 8 | 92 | | | | 100 |
| 31 BW | Y | 2 | 95 | 3 | | | | 100 |
| | 7 | | 5 | 90 | 2 | 3 | | 100 |
| | 8 | | 3 | 93 | 2 | 2 | | 100 |
| | 9 | | 5 | 95 | | | | 100 |
| | 10 | | 6 | 92 | 1 | 1 | | 77 |
| | 11 | | 5 | 95 | | | | 100 |
| 32 BW | Y | 2 | 94 | 2 | 2 | | | 100 |
| | 7 | 2 | 4 | 94 | | | | 66 |
| | 8 | | 4 | 95 | 1 | | | 82 |
| | 9 | | 7 | 90 | 3 | | | 100 |
| | 10 | * | | | | | | |
| | 11 | | 9 | 87 | 4 | | | 23 |

Figure 1A:
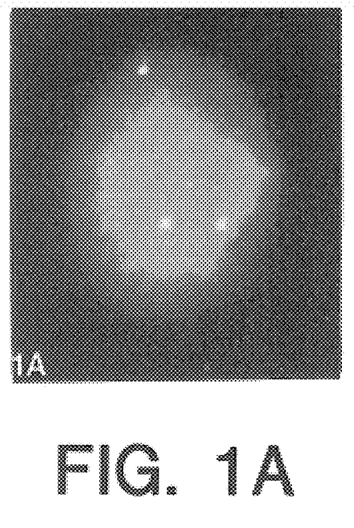
Figure 1B:
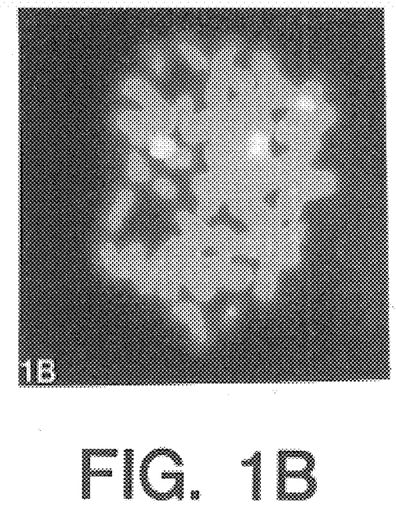
Figure 1C:
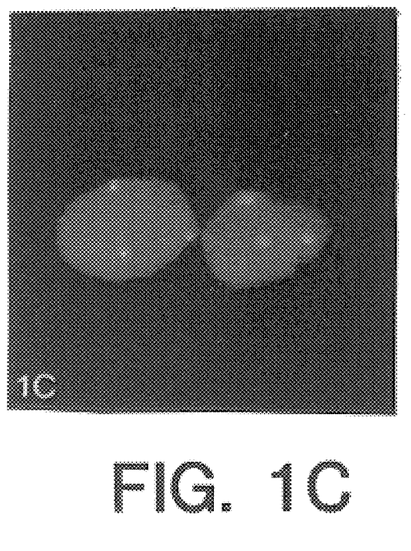
FIG. 1C shows both chromosome 7 and 8 probes in a cell isolated from urine.
Figure 1D:
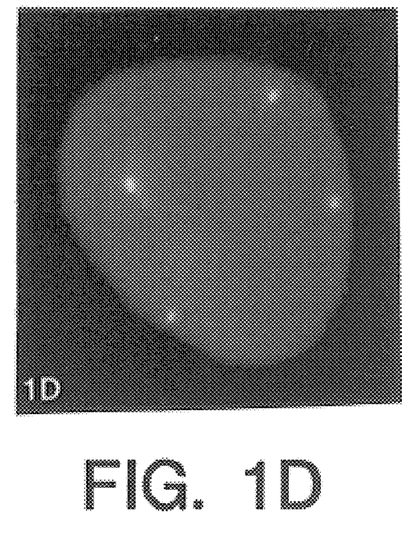
FIG. 1D shows both chromosome 7 and 8 probes in a cell isolated from bladder washings.
Figure 2:
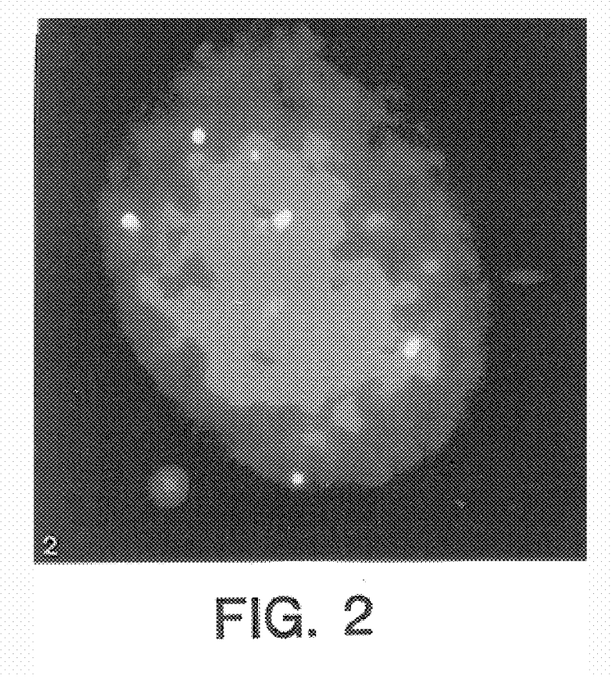
FIG. 2 illustrates the signal pattern obtained using a centromeric probe for chromosome 7, showing pentasomy of that chromosome.
Figure 3:
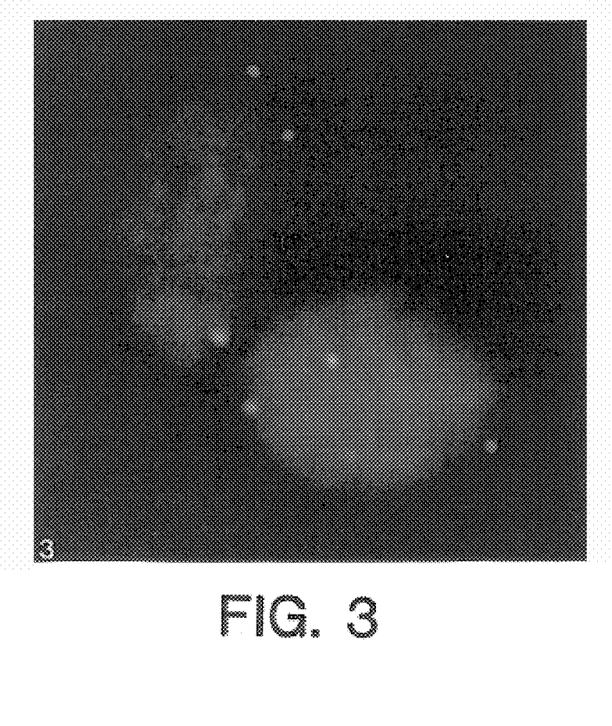
FIG. 3 illustrates the signal pattern obtained using a centromeric probe for chromosome 8, showing trisomy of that chromosome.
Figure 4A:
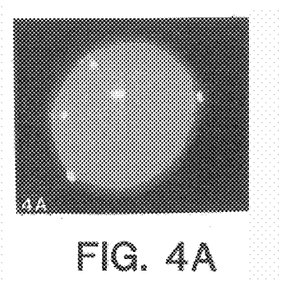
FIGS. 4A–4C illustrates the signal pattern obtained using a centromeric probe for chromosome 7 (4A–B) or chromosome 8 (4C).
Figure 4B:
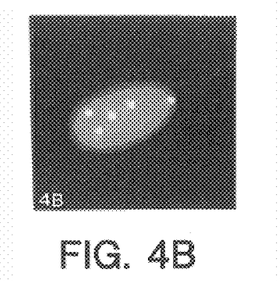
Figure 4C:
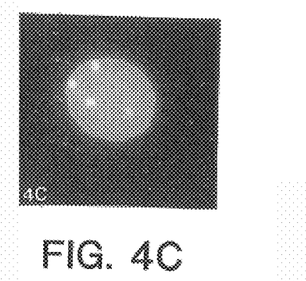
Figure 5A:
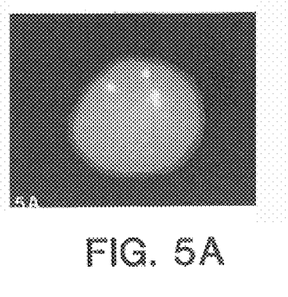
FIGS. 5A–5C illustrates the signal pattern obtained using a centromeric probe for chromosome 8 in cells obtained from a tumor (5A), bladder washing (5B) and urine (5C), showing trisomy of that chromosome.
Figure 5B:
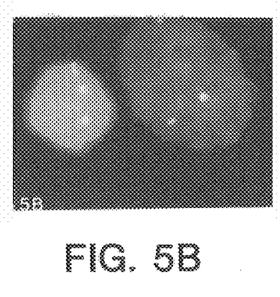
Figure 5C:
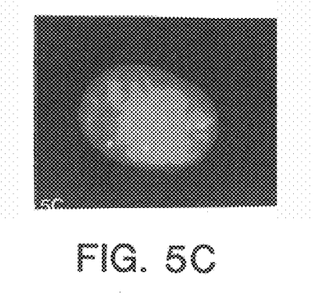

Some of the results obtained are depicted in FIGS. 1–5. FIG. 1A shows the trisomy 7 detected in patient 8. FIG. 1B shows trisomy 8. FIGS. 1C and D show the signals obtained from two probes (chromosomes 7 (red signal) and 8 (blue signal)) in cells obtained from the urine sample (1C) and bladder washing sample (1D) of patient 8. FIG. 2 shows pentasomy 7 detected in a cell isolated from the urine sample of patient 12. FIG. 3 shows trisomy 8 detected in a cell isolated from the urine sample of patient 5. FIG. 4A shows pentasomy 7 detected in a left tumor cell from patient 4. FIG. 4B shows pentasomy 7 detected in a cell isolated from bladder washing from patient 4. FIG. 4C shows trisomy 8 (possibly tetrasomy 8) detected in a cell isolated from urine from patient 4. FIGS. 5A–C show trisomy 8 in cells obtained from a tumor (5A), bladder washing (5B) and urine (5C), from patient 1.

It can be seen that urine samples appropriately collected and processed yield FISH results comparable to those of cultured or uncultured tissue cells. Since bladder cancers have a hyperdiploid chromosome complement, the situation can be easily detected by FISH using the appropriate probes.

Using the foregoing methods, a very high correspondence of FISH results between urine and bladder washings and between urine and tumor tissue cells were observed. Even when the cytogenetic findings were normal, FISH analyses of the tumor cells and urine revealed abnormalities not detected by simple microscopic analysis.

It is evident from the foregoing that FISH analysis of urine and bladder washings is a powerful tool which can be used in the establishment of the diagnosis and recurrence of bladder cancer. The reliability of the results is not only based on comparisons with those obtained in control subjects, but often also on the presence of more than one karyotypic change in any given case. Thus, the presence of two or more abnormalities in the same sample is almost certain to be indicative of the presence of cancer cells.

The use of the foregoing methods can alert the urologist on the presence of possible tumor cells in urine and bladder washings in bladder cancer and particularly in cases of carcinoma-in-situ. Finally, because collection of samples, particularly urine, is simple, monitoring can be performed more often, thus improving detection and management of bladder cancer.

REFERENCES CITED

1. Sandberg, A. A.: Chromosome changes in bladder cancer: Clinical and other correlations. Cancer Genet Cytogenet 19:163–175, 1986.
2. Sandberg, A. A., Berger, C. S.: Reviews on Chromosome Studies in Urological Tumors. II. Cytogenetics and Molecular Genetics of Bladder Cancer. J.Urol. 1993 (in press).
3. Gibas, Z., et al., Non-Random chromosomal changes in transitional cell carcinoma of the bladder. Cancer Res. 44:1257–1264, 1984.
4. Hopman A. H. N., et al.,: Numerical chromosome 1,7,9 and 11 aberrations in bladder cancer detected in situ hybridization. Cancer Res. 51:644–651, 1991.
5. Hopman A. H. N., et al.,: In situ hybridization as a tool to study numerical chromosome aberrations in solid bladder tumors. Histochemistry 89:307–316, 1988.
6. Hopman A. H. N., et al.,: Detection of numerical chromosome aberrations in bladder cancer by in situ hybridization. Amer.J.Pathol. 135:1105–1118, 1989.
7. Hopman A. H. N., et al.,: Detection of numerical chromosome aberrations using in situ hybridization in paraffin sections of routinely processed bladder cancers, Mod. .Pathol. 4:503–513, 1991.
8. Limon, et al.: Application of long-term collagenase disaggregation for the cytogenetic analysis of human solid tumors. Cancer Genet. Cytogenet. 23:305–313, 1986.
9. ISCN: Guidelines for Cancer Cytogenetics, Supplement to An International System for Human Cytogenetic Nomenclature, F. Mitelman (ed); S. Karger, Basel 1991.
10. Pinkel, et al.: Cytogenetic analysis using quantitative, high sensitivity fluorescense hybridization. Proc.Natnl.Sci., USA 83:2934–2938, 1986.

11. Berger, et al.: Chromosomes in kidney, ureter and bladder cancer. Cancer Genet Cytogenet 23:1–24, 1986.
12. Atkin, et al.: Cytogenetic study of ten carcinoma of the bladder: Involvement of chromosomes 1 and 11. Cancer Genet Cytogenet 15:253–268, 1985.
13. Smeets, et al.: Chromosomal analysis of bladder cancer: III. Non-random alterations. Cancer Genet Cytogenet 29:29–41, 1987.
14. Wang, et al.: Nonrandom changes of chromosome 10 in bladder cancer: detection by FISH to interphase nuclei. Cancer Genet Cytogenet (in press) 1993.
15. Waldman, et al.: Centromeric copy number of chromosome 7 is strongly correlated with tumor grade and labeling index in human bladder cancer. Cancer Res 51:3807–3813, 1991.
16. Poddighe, et al.: Structural chromosomes 1 aberrations in transitional cell carcinoma of the bladder. Interphase cytogenetics combining a centromeric, telomeric and library DNA-probe. Cancer Res 52:4929–4934, 1992.
17. Nederlof, et al.: Detection of chromosome aberrations in interphase tumor nuclei by nonradioactive in situ hybridization. Cancer Genet Cytogenet 42:87–98.
18. Smeets, et al.: Tissue specific markers in flow cytometry of urological cancers. III. Comparing chromosomal and flow cytometric DNA analysis of bladder tumors. Int J Cancer 39:304–310, 1987.
19. Sidransky, et al.: Identification of p53 gene mutations in bladder cancers and urine samples. Science 252:706–709, 1991.

What is claimed is:

1. A non-invasive method of screening for bladder cancer or bladder carcinoma in situ associated with chromosomal aneuploidy in humans, comprising the steps of:
    a) performing in situ hybridization on cells obtained from the voided urine or bladder washing of a human patient by contacting the cells under hybridization conditions with at least one detectable nucleic acid probe which will selectively hybridize to one aneuploid chromosome in the cells;
    b) detecting whether the probe hybridizes; and
    c) comparing the results in step b) to a predetermined in situ hybridization pattern obtained from normal cells, wherein the bladder cancer or bladder carcinoma in situ is detected if the results obtained in step b) are different from the predetermined pattern. pattern.

2. The method of claim 1, wherein the nucleic acid probe is an alpha centromeric probe.

3. The method of claim 1, wherein a bladder cancer or bladder carcinoma in situ cell is detected by having a numerical change in at least one chromosome selected from the group consisting of 1, 7, 8, 9, 10, 11, Y and X.

* * * * *